United States Patent [19]

Teicher et al.

[11] Patent Number: 5,502,214

[45] Date of Patent: Mar. 26, 1996

[54] 1,2-BENZOQUINONES AND METHODS FOR MAKING AND USING SAME

[75] Inventors: Beverly A. Teicher, Needham, Mass.; Zhen-Dong Huang, Shanghai, China

[73] Assignee: Dana Farber Cancer Institute, Boston, Mass.

[21] Appl. No.: 93,763

[22] Filed: Jul. 19, 1993

[51] Int. Cl.$^6$ .................. C07D 205/00; C07D 229/00; C07C 50/02

[52] U.S. Cl. .................. 548/950; 548/961; 548/518; 548/343.5; 548/365.1; 548/562; 552/291; 544/111; 544/336; 544/359

[58] Field of Search .................. 552/291; 548/963, 548/961, 950, 518

[56] References Cited

U.S. PATENT DOCUMENTS 4,879,243  11/1989  Mura et al. .................. 436/63

FOREIGN PATENT DOCUMENTS 762723  10/1954  United Kingdom.
2111981  7/1983  United Kingdom.

OTHER PUBLICATIONS

Websters II, 1984, p. 1078.
J. S. Driscoll et al., "Structure–Activity Relationships Among Antitumour Quinones", Martinus Nijhoff Publishers, pp. 135–148 (1983).
J. S. Driscoll et al., *Cancer Chemotherapy Reports Part 2*, 4(2):1–27 (1974).
F. Chou et al., *Journal of Med. Chemistry*, 19(11):1302–1308 (1976).
J. Hartley et al., *Biochemistry*, 30:11719–11724 (1991).
Y. Itoh et al., *Bulletin of the Chemical Society of Japan*, 52(7):2169–2170 (1979).
V. Voleva et al., *Chemical Abstracts*, 106:32468g (1987).
W. Gauss et al., *Chemical Abstracts*, 53:10163 (1959).
G. Domagk et al., *Chemical Abstracts*, 48:11658c (1954).
C. Lee et al., *Biochemistry*, 31:3019–3025 (1992).
G. Powis, *Free Radical Biology & Medicine*, 6:63–101 (1989).
S. Hayashi et al., *UDS*, 11(7):948–951 (1963).
S. Hayashi et al., *GANN*, 54:381–390 (1963).

*Primary Examiner*—Rebecca Cook
*Attorney, Agent, or Firm*—David G. Conlin; Ronald I. Eisenstein; Peter F. Corless

[57] ABSTRACT

The present invention relates to 1,2-benzoquinones; methods of preparation of 1,2-benzoquinones that include preparation of 4,5-substituted-1,2-benzoquinones in a one-pot reaction; and methods of treatment and pharmaceutical compositions that utilize or comprise one or more of such benzoquinones.

34 Claims, No Drawings

1,2-BENZOQUINONES AND METHODS FOR MAKING AND USING SAME

BACKGROUND OF THE INVENTION

1. Field of the Invention

The present invention relates to novel 1,2-benzoquinones, methods of preparation of 1,2-benzoquinones, and methods of treatment and pharmaceutical compositions that utilize or comprise one or more of such benzoquinones.

2. Background Art

The quinone moiety occurs abundantly in nature playing vital roles in normal biochemical processes and in the action of many cytotoxins. See, e.g., P. J. O'Brien, Molecular mechanisms of quinone cytotoxicity, *Chem.-Biol. Interactions*, 80:1–41 (1991); H. Nohlet al., Quinones in biology: Functions in electron transfer and oxygen activation, *Adv. Free Rad. Biol. Med.*, 2:211–279 (1986); W. Kersten, Inhibition of RNA synthesis by quinone antibiotics, *Prog. Mol. Subcell. Biol.*, 2:48–57 (1971); C. Olenick et al., Bactericidal action of a 2-hydroxy-3-alkyl-1,4 naphthoquinone, *Ann. N.Y. Acad. Sci.*, 235:542–552 (1974); S. Rich, In: *Fungicities, An Advanced Treatise*, Torgeson, D. C., Ed.; Academic Press: New York, 1968; Y. Martin et al., Relationship between physical properties and antimalarial activities of 1,4-naphthoquinone, *J. Med. Chem.*, 16:1089–1093 (1973); T. Eisner et al., Defense mechanisms of anthropoids, 57, Chemistry of defensive secretions of bombardier beetles, *J. Insect. Physiol.*, 23:1383–1386 (1977); J. Driscoll et al., Structure-antitumor activity relations among quinone derivatives, *Cancer Chemother. Rep.*, 4(part 2):1–27 (1974); and G. Powis, Free radical formation by antitumor quinones, *Free Rad. Biol. Med.*, 6:63–101 (1989).

More than 1000 naturally occurring quinones have been tested for antitumor activity several of these including doxorubicin, daunorubicin and mitomycin C are in current clinical use. Aziridinyl-1,4-benzoquinones were among the earliest rationally designed synthetic anticancer agents. G. Powis, Metabolism and reactions of quinoid anticancer agents, *Pharmacol. Ther.*, 35:57–162 (1987); and T. Deeley, A clinical trial of synkavit in the treatment of carcinoma of the bronchus, *Br. J. Cancer*, 16:387–389 (1980). Of these, diaziquinone [3,6-bis(ethylcarboxyamino)-2,5-diaziridinyl-1,4-benzoquinone [AZQ; NSC-182986] is currently in clinical use primarily for treatment of brain tumors.

Relative to 1,4-benzoquinone derivatives, the 1,2-benzoquinone derivatives have been reported to be much more difficult to prepare even in moderate yield. Indeed, there has been little exploration of 1,2-benzoquinone compounds despite the potential for 1,2-benzoquinones to form highly reactive species that could crosslink DNA and thus have potential as antitumor agents.

It thus would be desirable to have improved means for obtaining 1,2-benzoquinone compounds. It also would be desirable to have new 1,2-benzoquinone compounds, particularly 1,2-benzoquinone compounds that are useful as antitumor agents.

SUMMARY OF THE INVENTION

The present invention provides novel means for preparation of 1,2-benzoquinones. The method of the invention in general comprises contacting a catechol with a metal containing compound, preferably a compound containing Fe, Co, Ni, Cu, Zn or Ga, to form a 1,2-benzoquinone. The invention also provides methods for preparation of substituted 1,2-benzoquinones comprising contacting a catechol with a metal containing compound as described above in the presence of a nucleophilic reagent to provide a 1,2-benzoquinone substituted at the 4 and/or 5 positions. These oxidation and addition reactions can be conducted without isolation of an oxidized intermediate, i.e. in a single step "one-pot" synthesis, to provide a substituted 1,2-benzoquinone in high yields. A variety of 1,2-benzoquinones can be prepared in accordance with this method, including compounds of the following Formula I:

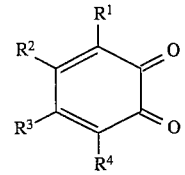

wherein $R^1$ and $R^4$ are each independently hydrogen, halogen, cyano, substituted or unsubstituted alkyl, substituted or unsubstituted alkenyl, substituted or unsubstituted alkoxy, substituted or unsubstituted aminoalkyl, or substituted or unsubstituted thioalkyl; and $R^2$ and $R^3$ are each independently hydrogen, substituted or unsubstituted alkyl, substituted or unsubstituted alkenyl, substituted or unsubstituted alkoxy, substituted or unsubstituted aminoalkyl, substituted or unsubstituted thioalkyl, substituted or unsubstituted alkylsulfoxide, substituted or unsubstituted sulfonoalkyl, substituted or unsubstituted alkanoyl, substituted or unsubstituted alkylcarboxyamino, or a substituted or unsubstituted heteroaromatic or heteroalicyclic group having 1 to 3 rings, 3 to 8 ring members in each ring and 1 to 3 hetero atoms.

In another aspect of the invention, novel 1,2-benzoquinones are provided, including compounds of the following Formula II:

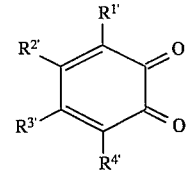

wherein $R^{1'}$ and $R^{4'}$ are each independently hydrogen, halogen, cyano, substituted or unsubstituted alkyl, substituted or unsubstituted alkenyl, substituted or unsubstituted alkoxy, substituted or unsubstituted aminoalkyl, or substituted or unsubstituted thioalkyl;

$R^{2'}$ and $R^{3'}$ are each independently substituted or unsubstituted alkyl, substituted or unsubstituted alkenyl, substituted or unsubstituted alkoxy, substituted or unsubstituted aminoalkyl, substituted or unsubstituted thioalkyl, substituted or unsubstituted alkylsulfoxide, substituted or unsubstituted sulfonoalkyl, substituted or unsubstituted alkanoyl, substituted or unsubstituted alkylcarboxyamino, or a substituted or unsubstituted heteroaromatic or heteroalicyclic group having 1 to 3 rings, 3 to 8 ring members in each ring and 1 to 3 hetero atoms; and pharmaceutically acceptable salts thereof;

with the proviso that $R^{2'}$ and $R^{3'}$ are not the same group and are other than hydrogen or unsubstituted alkyl having from 1 to 3 carbon atoms when $R^{1'}$ and $R^{4'}$ are both hydrogen or are both unsubstituted alkyl and $R^{2'}$ or $R^{3'}$ is substituted or unsubstituted alkoxy having 1 to 3 carbon atoms, substituted or unsubstituted aminoalkyl having 1 to 4 carbon atoms, or a substituted or substituted alicyclic group that contains a nitrogen ring atom and from 1 to 3 carbon ring atoms.

A preferred group of benzoquinones of the invention are compounds of Formula II as defined above except with the proviso that $R^{2'}$ and $R^{3'}$ are not the same group and are each other than hydrogen or unsubstituted alkyl when $R^{2'}$ or $R^{3'}$ is substituted or unsubstituted alkoxy, substituted or unsubstituted aminoalkyl, or a substituted or substituted alicyclic group that contains a nitrogen ring atom.

A particularly preferred group of benzoquinones of Formula II are compounds of the following Formula IIa:

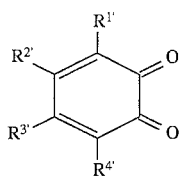

IIa wherein $R^{1''}$ and $R^{4''}$ are each independently hydrogen, halogen, cyano, substituted or unsubstituted alkyl, substituted or unsubstituted alkenyl, substituted or unsubstituted alkoxy, substituted or unsubstituted aminoalkyl, or substituted or unsubstituted thioalkyl;

$R^{2'}$ and $R^{3'}$ are each independently hydrogen, substituted or unsubstituted alkyl, substituted or unsubstituted alkenyl, substituted or unsubstituted thioalkyl, substituted or unsubstituted alkylsulfoxide, substituted or unsubstituted sulfonoalkyl, substituted or unsubstituted alkanoyl, substituted or unsubstituted alkylcarboxyamino, or a substituted or unsubstituted heteroaromatic group having 1 to 3 rings, 3 to 8 ring members in each ring and 1 to 3 hetero atoms; and pharmaceutically acceptable salts thereof.

Compounds of the invention, including compounds of Formula II, will have utility in therapeutic applications, particularly in antitumor therapies, e.g. to treat an animal bearing susceptible tumors. Accordingly, the present invention includes methods which comprise using one or more compounds to treat tumors in a mammal, particularly a human. Compounds of the invention also will be useful synthetic intermediates to form other compounds including bifunctional alkylating agents that have potential antitumor applications.

The invention further provides pharmaceutical compositions that comprise one or more compounds of the invention and a suitable carrier.

DETAILED DESCRIPTION OF THE INVENTION

The method of the invention in general comprises mixing of a catechol, an oxidizing agent and a metal containing compound to provide a 1,2-benzoquinone, Preferably the reaction mixture further includes a nucleophilic compound which undergoes conjugate addition to provide substitution at the 4 and/or 5 positions of the benzoquinone thereby yielding a substituted 1,2-benzoquinone in a single step (one-pot) reaction from a catechol.

Preferred metal complexing compounds used in the reaction include compounds that comprise Fe, Cu, Ni, Zn, or Ga. Ru, Rh, or Pd also can be employed, alone or in combination with the preferred metal compounds, but these higher atomic number metals are likely to be more inert and hence less preferred. Preferably the metal complexing compound is an organic (e.g., an acetate) or inorganic metal salt that can form a complex, particularly an ionic complex, with a semiquinone intermediate as discussed below. Copper compounds are particularly preferred metal containing compounds including copper I and II species such as copper (II) acetate, copper (I) chloride, copper (I) bromide and copper iodide.

In an alternative embodiment of the invention, in the synthetic method described herein a metal complexing compound that contains Mn is employed to form benzoquinones of Formula I as defined above but where substituents $R^2$ and $R^3$ are $R^{2''}$ and $R^{3''}$, wherein $R^{2''}$ and $R^{3''}$ are independently hydrogen or substituted or unsubstituted alkyl, alkenyl, aminoalkyl, thioalkyl, alkylsulfoxide, sulfonoalkyl, alkanoyl, alkylcarboxyamino, or a heteroaromatic or heteroalicyclic group.

A number of oxidizing agents can be employed in the reaction. The oxidant preferably does not induce decomposition or polymerization of other reagents or the formed benzoquinone. Hence a relatively mild oxidant is preferably used such as sodium iodate, preferably with dry oxygen gas being added to the reaction mixture. Fremy's salt (potassium nitrosodisulfonate) also will be suitable. Ammonium nitrate coated on silica also can be employed, but it has been found that this reagent may not form a homogeneous mixture in at least some reaction solutions and for such reasons is less preferred. While more reactive oxidants such as sodium dichromate, chromic acids and silver oxide could be employed, such reagents can promote decomposition and polymerization of the reactive 1,2-benzoquinones once formed and, hence, these strong oxidants are less preferred for use in the synthetic methods of the invention.

It is also preferred that the reaction mixture contain a drying agent such as anhydrous magnesium sulfate, anhydrous sodium sulfate or suitable molecular sieves (4 or 5 angstroms) to absorb water formed in situ during the course of the reaction.

A variety of nucleophilic reagents can be used in the reaction to provide substituents at the 4 and/or 5 position of the benzoquinone. Preferred nucleophiles include heteroatom-containing compounds, particularly compounds that contain one or more N, O or S atoms such as substituted or unsubstituted aminoalkyl groups including dialkylamino groups and halo-substituted aminoalkyl groups, substituted or unsubstituted thioalkyl groups, substituted or unsubstituted alkoxy groups, or a substituted or unsubstituted heteroaromatic or heteroalicyclic group having 1 to 3 rings, 3 to 8 ring members in each ring and 1 to 3 hetero atoms.

Other suitable nucleophiles includes alkyl groups substituted with electron-attracting substituents such as carboxy-substituted aliphatic compounds and nitroalkanes. Nucleophiles stabilized by multiple electron-attracting groups are particularly suitable, e.g., enolates of malonate esters or beta-keto esters. Organometallic reagents also will be suitable nucleophiles, e.g., organolithium and organocopper reagents such as LiCu(CH=CH$_2$)$_2$, Ph$_2$CuLi and n-BuCu. See F. S. Alvarez, et al., *J. Am. Chem. Soc.*, 94:7823 (1972); M. Suzuki, et al., *Tetrahedron Letters*, 1247 (1980); N. Finch, et al., *J. Org. Chem.*, 39:1118 (1974).

When employing a nucleophilic reagent to provide substitution of the 4 and/or 5 positions of the 1,2-benzoquinone, the reaction solution should contain a suitable base to catalyze the Michael reaction. Suitable basic catalysts include, e.g., organic amines such as triethylamine and pyridine.

The oxidation and addition reactions are preferably conducted at below room temperature, more preferably at from about −40° C. to 15° C., still more preferably from about −20° C. to 10° C., even more preferably from about −10° C. to 5° C., and most preferably from about −5° C. to 0° C.

Reaction completion can be readily determined, e.g., by thin layer chromatography. As will be appreciated by those skilled in the art, suitable reaction times will vary with a number of factors such as reaction temperature and reactivity of the metal complexing compound, catechol and nucleophilic reagent. It has been found that using a copper complexing compound, an amine nucleophilic reagent and a reaction temperature of −5° C. to 0° C., the reaction proceeds to completion in about 2 to 20 hours with stirring.

The catechol, oxidant, metal containing compound and nucleophilic reagent are typically dissolved or dispersed in a suitable solvent during the oxidation and addition reaction. A variety of solvents will be suitable including non-polar solvents such as, e.g., chloroform, methylene chloride and acetone and mixtures thereof. The skilled artisan can readily determine suitable solvent(s) based on the constituents of a particular reaction. If the oxidation and substitution reactions are conducted at higher temperatures, e.g., greater than about 0° C., preferably the reaction solution is comparatively dilute and isolated from light to avoid polymerization of the benzoquinone once it is formed.

Typically the metal containing compound and oxidant are added to a cooled solution of the catechol followed by addition of the nucleophilic reagent to the reaction mixture. The reaction mixture is then suitably stirred, preferably at reduced temperature as discussed above, until reaction completion.

For preparation of monosubstituted compounds, i.e. 1,2-benzoquinones substituted at only the 4 or 5 positions, reaction conditions should be employed to promote the mono-substitution reaction rather than formation of disubstituted species. For instance, the reaction can be run at lower temperatures (e.g. less than 0° C.) in a dilute solution using a slight molar excess of the catechol relative to the nucleophilic reagent.

4,5-substituted-1,2-benzoquinones with differing substituents at the 4 and 5 positions (e.g., compounds of Formula I where $R^2$ and $R^3$ are each other than hydrogen and are different) can be suitably prepared by reaction of a formed 4,5-substituted-1,2-benzoquinone with about a molar equivalent of a nucleophilic reagent to displace a substituent at the 4 or 5 positions. For example, a 4,5-alkoxy-1,2-benzoquinone can be reacted with an amine, e.g. a primary amine such 2-chloroethylamine, to provide a 4-amino-5-alkoxy-1,2-benzoquinone.

Substituents at the 3 and 6 positions of a 1,2-benzoquinone (e.g., groups $R^1$ and $R^4$ of compounds of Formula I) can be provided by use of an appropriately substituted catechol as a starting material. Alternatively, once formed the 1,2-benzoquinone can be further reacted to provide 3,6-substituents. For example, 3,6-chlorination of a 1,2-benzoquinone should be possible by reaction of the benzoquinone with t-butyl hypochlorite in a suitable solvent such as methanol, or by other suitable reaction.

As discussed above, the synthetic methods of the invention can provide a 1–2-benzoquinone substituted at the 4 and/or 5 positions in high yields. For example, 1,2-benzoquinones substituted at the 4 and/or 5 positions can be prepared in yields from a catechol of about 20 mole percent or greater, more preferably about 40 mole percent or greater, still more preferably about 50 mole percent or greater, and even yields of about 60 mole percent or greater based on the catechol starting material.

Without wishing to be bound by any theory, it is believed the substituted 1,2-benzoquinones are formed via the methods of the invention by oxidation of the catechol via a two-electron transfer (either as a simultaneous two-electron transfer step or as two separate one-electron transfer steps) with a semiquinone intermediate which forms a stable complex with the metal containing compound or species thereof. The metal-1,2-semiquinone intermediate, which may exist as a monomer or dimer (i.e., the metal species can complex with one or two benzoquinone molecules) serves as a Michael acceptor for reaction with the nucleophilic reagent. Subsequent hydrolysis provides the 1,2-benzoquinone substituted at the 4 and/or 5 positions.

It is also believed that the metal-containing compound or species thereof serves as an electron acceptor in the oxidation reaction. Accordingly, preferred metal-containing compound are capable of serving as an electron acceptor in such oxidation reactions.

Suitable halogen substituent groups of compounds of the invention, including compounds of Formula I and II as defined above, include F, Cl, Br and I. Alkyl groups of 1,2-benzoquinones of the invention preferably have from 1 to about 12 carbon atoms, more preferably 1 to about 8 carbon atoms, still more preferably 1 to about 6 carbon atoms. As used herein, the term alkyl unless otherwise modified refers to both cyclic and noncyclic groups, although of course cyclic groups will comprise at least three carbon ring members. Straight or branched chain noncyclic alkyl groups are generally more preferred than cyclic groups, particularly branched chain groups such as isopropyl and t-butyl. Preferred alkenyl groups of compounds of the invention have one or more unsaturated linkages and from 2 to about 12 carbon atoms, more preferably 2 to about 8 carbon atoms, still more preferably 2 to about 6 carbon atoms. The term alkenyl as used herein refer to both cyclic and noncyclic groups, although straight or branched noncyclic groups are generally more preferred, particularly branched chain groups. Preferred alkoxy groups of benzoquinones of the invention include groups having one or more oxygen linkages and from 1 to about 12 carbon atoms, more preferably from 1 to about 8 carbon atoms, and still more preferably 1 to about 6 carbon atoms. Preferred thioalkyl groups of compounds of the invention include those groups having one or more thioether linkages and from 1 to about 12 carbon atoms, more preferably from 1 to about 8 carbon atoms, and still more preferably 1 to about 6 carbon atoms. Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms. Substituted and unsubstituted dialkylamino groups are particularly preferred, especially where each alkyl chain of the group has from 1 to about 6 carbon atoms. Preferred alkylsulfoxide of compounds of the invention have one or more sulfoxide groups, more typically one sulfoxide group, and from 1 to about 12 carbon atoms, more preferably 1 to about 8 carbon atoms, still more preferably 1 to about 6 carbon atoms. Preferred sulfonoalkyl groups of benzoquinones of the invention have one or more sulfono ($SO_2$) groups, more typically one or two sulfono groups, and from 1 to about 12 carbon atoms, more preferably 1 to about 8 carbon atoms, still more preferably 1 to about 6 carbon atoms. Preferred alkanoyl groups of compounds of the invention include groups having one or more carbonyl groups, more typically one or two carbonyl groups, and from 1 to about 12 carbon atoms, more preferably 1 to about 8 carbon atoms, still more preferably 1 to about 6 carbon atoms. Preferred alkylcarboxyamino groups include those groups of the formula —NHCOOR where R is substituted or unsubstituted alkyl having from 1 to about 10 carbon atoms, more preferably 1 to about 6 carbon atoms. Suitable heteroaromatic groups of compounds of the invention contain one or more N, O or S atoms and include, e.g., quinolinyl, pyridyl, pyrazinyl, indolyl, carbazoyl, furyl, pyrrolyl, thienyt, thiazolyl, aminothioazole such as 2-aminothiazole, pyrazole, oxazolyl, imidazolyl, indolyl, benzofuranyl, benzothiazol and pyridonal including 2-pyridonals and 4-pyridonals, particularly pyridonal substituted at one or more ring positions by moieties such as hydroxy, alkanoyl such as acetate, alkylaminocarbonyl having from 1 to about 8 carbon atoms and alkoxycarbonyl having from 1 to about 8 carbon atoms. Suitable heteroalicyclic groups of compounds contain one or more N, O or S atoms and include, e.g., aziridinyl, azetidinyl, tetrahydrofuranyl, tetrahydropyranyl, pyrrolidino, 1,2,3,6-tetrahydropyridino, piperazino, piperidinyl, morpholino and thiomorpholino.

Substituted moieties of 1,2-benzoquinones of the invention, including substituted $R^1$, $R^2$, $R^3$, $R^4$, $R^{1'}$, $R^{2'}$, $R^{3'}$, $R^{4'}$, $R^{1''}$, $R^{2''}$, $R^{3''}$ and $R^{4''}$ groups, may be substituted at one or more available positions by one or more suitable groups such as, e.g., halogen such as fluoro, chloro, bromo and iodo; cyano; hydroxyl; nitro; alkyl groups including those groups having 1 to about 12 carbon atoms or from 1 to about 6 carbon atoms, preferably noncyclic alkyl groups including branched chain groups such as isopropyl and t-butyl; alkenyl and alkynyl groups including groups having one or more unsaturated linkages and from 2 to about 12 carbon or from 2 to about 6 carbon atoms; alkylthio groups including those moieties having one or more thioether linkages and from 1 to about 12 carbon atoms or from 1 to about 6 carbon atoms; and, in at least preferred aspects of the invention, alkoxy groups having those having one or more oxygen linkages and from 1 to about 12 carbon atoms or 1 to about 6 carbon atoms; and aminoalkyl groups such as groups having one or more N atoms (which can be present as primary, secondary and/or tertiary N groups) and from 1 to about 12 carbon atoms or from 1 to about 6 carbon atoms.

Particularly preferred substituent groups of compounds of the invention, including compounds of Formulas I and II, include nitrogen containing groups including aminoalkyl, alkylcarboxyamino and nitrogen-containing heteroaromatic and heteroalicyclic groups. Preferred nitrogen-containing cyclic groups include those moieties that have one or two heteroatoms, e.g. one or two N, O, or S atoms. Preferably 1,2-benzoquinone compounds of the invention are substituted at the 4 and/or 5 positions by groups other than hydrogen.

Compounds specifically excluded from Formula II are 4,5-di($C_{1-3}$alkoxy)-1,2-benzoquinone including 4,5-dimethoxy-1,2-benzoquinone and 3,6-di(t-butyl)-4,5-dimethoxy-1,2-benzoquinone; 4-aziridinyl-5-$C_{1-3}$alkyl-1,2-benzoquinone including 4-aziridinyl-5-methyl-1,2-benzoquinone; 4,5-diazridinyl-1,2-benzoquinone; 4-phenylamino-1,2-benzoquinone and 4,5-phenylamino-1,2-benzoquinone including 4-phenylmethylamino-1,2-benzoquinone; di(di-$C_{1-3}$alkylamino)-1,2-benzoquinone including 4,5-di(dimethylamino)-1,2-benzoquinone; 4-$C_{1-4}$alkylamino-1,2-benzoquinone including 4-dimethylamino-1,2-benzoquinone; 4-$C_{1-3}$alkoxy-1,2-benzoquinone including 4-methoxy-1,2-benzoquinone and 3,6-di(t-butyl)-4-methoxy-1,2-benzoquinone.

It has been found that compounds of the present invention exhibit cytotoxicity under at least several environmental conditions as well as in vivo antitumor activity. Accordingly, the invention provides methods of reducing susceptible cancer cells, e.g. a solid tumor or a disseminated tumor such as leukemia cells, by contacting such cancer cells with an effective cancer cell reducing amount of one or more compounds of the invention. Susceptible cancer cells can be readily determined including by means of protocols such as those of Examples 6 and 7 which follow. More specifically, compounds of the invention, including compounds of Formula II, will be active against murine tumors. Murine tumors include, e.g., lymphocytic leukemia P388/0 and L1210, malanotic melanoma B16, P815 mastocytoma fibrosarcoma, and Lewis lung carcinoma. Compounds of the invention will have activity against other cancer cells, e.g. brain, lung, ovary, breast, renal, pancreatic, melanoma and/or colon tumors of a mammal such as a human.

Thus the compounds of the present invention, particularly compounds of Formula II, are useful as pharmaceuticals for the treatment of mammals, including humans, particularly for the treatment of mammals having cancer cells, e.g. a disseminated and/or solid tumor susceptible to the compounds of the invention. Thus, the invention provides a method for the treatment of susceptible cancer cells, such as a disseminated or solid tumor, in mammals including humans, the method comprising administration of an antitumor effective amount of one or more compounds of the invention in a pharmaceutically useful form, once or several times a day or other appropriate schedule, orally, rectally, parenterally (particularly intravenously), topically, etc.

For such treatment, the compounds of the invention are administered in effective amounts and in appropriate dosage form ultimately at the discretion of the medical or veterinary practitioner. For example, as known to those skilled in the art, the amount of 1,2-benzoquinone required to be pharmaceutically effective will vary with a number of factors such as the mammal's weight, age and general health, the efficacy of the particular compound and formulation, route of administration, nature and extent of the condition being treated, and the effect desired. The total daily dose may be given as a single dose, multiple doses, or intravenously for a selected period. Efficacy and suitable dosage of a particular compound can be determined by known methods including through use of the protocols of Examples 6 and 7 which follow. More particularly, for treatment of a tumor in a mammal such as a human, particularly when using more potent compounds of the invention, a suitable effective dose of the 1,2-benzoquinone will be in the range of 0.1 to 100 milligrams per kilogram body weight of recipient per day, preferably in the range of 1 to 10 milligrams per kilogram body weight of recipient per day. The desired dose is suitably administered once daily, or as several sub-doses, e.g. 2 to 4 sub-doses administered at appropriate intervals through the day, or other appropriate schedule. Such sub-doses may be administered as unit dosage forms, e.g., containing from 0.2 to 200 milligrams of compound(s) of the invention per unit dosage, preferably from 2 to 20 milligrams per unit dosage.

The 1,2-benzoquinones of the present invention may be suitably administered to a subject as a pharmaceutically acceptable salt. Such salts can be prepared in a number of ways. For example, where the compound comprises a basic group such as an amino group, salts can be formed from an organic or inorganic acid, e.g. hydrochloride, sulfate, hemisulfate, phosphate, nitrate, acetate, oxalate, citrate, maleate, etc. Where the compound comprises a carboxy group, pharmaceutically acceptable salts include those formed form alkali metal salts, e.g. a sodium salt.

The therapeutic compound(s) may be administered alone, or as part of a pharmaceutical composition, comprising at least one compound of the invention together with one or more acceptable carriers thereof and optionally other therapeutic ingredients, e.g., other antitumor agents. The carrier(s) must be "acceptable" in the sense of being compatible with the other ingredients of the formulation and not deleterious to the recipient thereof.

The compositions include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes, and may be prepared by any methods well known in the art of pharmacy.

Such methods include the step of bringing into association the to be administered ingredients with the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for topical administration to the skin may be presented as ointments, creams, gets and pastes comprising one or more compounds of the present invention and a pharmaceutically acceptable carrier. A suitable topical delivery system is a transdermal patch containing the ingredient to be administered.

Compositions suitable for rectal administration may be presented as a suppository with a suitable base comprising, for example, cocoa butter or a salicylate.

Compositions suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above the formulations of this invention may include other agents conventional in the art having regard to the type of formulation in question, for example, those suitable for oral administration may include flavoring agents.

Due to their reactivity, the 1,2-benzoquinones of the invention, including compounds of Formula II, will be useful as crosslinking agents in a variety of applications, e.g., in forming polymerized coatings. The benzoquinones of the invention also will have utility as electron transfer agents and thus will be useful in analytical determinations. See U.S. Pat. No. 4,879,243 to Mura et al. for a description of such electron transfer agent use.

All documents mentioned herein are incorporated herein by reference.

The present invention is further illustrated by the following examples. These examples are provided to aid in the understanding of the invention and are not to be construed as limitations thereof.

GENERAL COMMENTS

In the following examples, melting points (mp) were determined with a Fisher-Johns melting point apparatus. I.R. spectra were determined on a Perkin-Elmer 781 infrared spectrophotomer as potassium bromide pellets. U.V. spectra were determined on a Beckman DU-70 spectrophotometer. $^1$HNMR spectra were obtained in $CDCl_3$ with tetramethylsilane as an internal reference using a EM360L NMR spectrometer (Varian). Analytical thin layer chromatography (TLC) was carried out on TLC aluminum sheets of silica gel 60F254 pre-coated (EM Science). Column chromatography was performed by using silica gel [60–200 Mesh (Baker Analyzed)] as the chromatographic adsorbent. Chemicals and solvents were purchased from Aldrich Chemical Co. (St. Louis, Mo.). Dichloromethane was dried over anhydrous calcium chloride and redistilled, stored over molecular sieves 4Å, triethylamine was dried over sodium hydroxide and redistilled before using. Anhydrous magnesium sulfate was dried in an oven at 110° C. for 10 hours prior to use. Ethylenimine was synthesized from according to the method of Reeves et al., *JACS*, 73:3522 (1951). Elemental analyses were performed by Quantitative Technologies, Inc., Bound Brook, N.J. 08805. 4,5-Dimethoxy-1,2-benzoquinone used in the examples was prepared by methods of Itoh, Y. et al., *Bull. Chem. Soc. Jpn.*, 5.2:2169–2170 (1979).

EXAMPLE 1

Method A: Preparation of 4,5-aziridinyl-1,2-benzoquinone

A solution of catechol (110 mg, 1 mmol) in dried dichloromethane (25 ml) was cooled at 0° C. and well stirred in an ice bath in a 3-neck round-bottomed flask equipped with a condenser, a cylindrical funnel protected by drying tube (calcium chloride) and a glass tube which was connected to an oxygen cylinder through a drying tube (silica gel). To this solution the following reagents were added: anhydrous magnesium sulfate (3 g), copper (II) acetate (181.69 mg, 1 mmol) and sodium iodate (792 mg, 4 mmol). After stirring for 10 minutes a solution of ethylenimine (0.41 ml, 8 mmol) and triethylamine (0.56 ml, 4 mmol) in dichloromethane (15 ml) were added dropwise from the cylindrical funnel into the reaction mixture, at the same time as the addition of the amine, oxygen was introduced through the glass tube. The reaction mixture was then maintained with bubbling oxygen and stirring at 0° C. for 18–20 hours until the reaction was complete as determined by disappearance of the catechol on TLC. Over the course of the reaction, the reaction solution changed color from light blue to deep-green and at last to dark red. The reaction mixture was filtered and washed with dichloromethane. Concentration of the solvent under vacuum with temperature maintained below 25° C. gave a black red solid which was extracted with chloroform and washed with ice water (40 ml), 10% acetic acid (2–3 ml) and distilled water saturated with sodium chloride (20–30 ml), then dried over magnesium sulfate. Evaporation of the extracting solvent gave the crude product. Column chromatography with chloroform elution afforded the title compound, 4,5-aziridinyl-1,2-benzoquinone (119.6 mg, 62.88% yield) as deep red needles from $CH_2Cl_2$/acetone (1:1), mp 144°–145° C. (decomp); Anal. Calcd. for $C_{10}H_{10}N_2O_2$: C,63.14; H,5.30, N,14.41%. Found: C,62.75; H,5.01; N,14.40%. I.R. $\upsilon$max 3080, 3000, 2920, 1640, 1550, 1370, 870 $cm^{-1}$; U.V. $\lambda$max (95% EtOH) 220 nm (log $\epsilon$4.21), 264 (3.68) 344 (4.11); $^1$HNMR ($CDCl_3$) $\delta$, 2.3 (s, 8H, 4- and 5-aziridinyl), 5.8 (s, 2H, 3,6-H).

Method B

Starting from 4,5-methoxy-1,2-benzoquinone (prepared by methods of Y. Itoh et al., *Bull. Chem. Soc. Japan*, 52(7):2169–2170 (1979), the synthetic method was generally followed as described in Method A above, but without use of oxygen gas or the oxidizing agent sodium iodate. The nucleophilic substitution reaction of ethylenimine was carried out for 19 hours at 0° C. The product mixture consisted of 4,5-aziridinyl-1,2-benzoquinone (16% yield) and 4-aziridinyl-5-methoxy-1,2-benzoquinone (24% yield) calculated by $^1$HNMR. These two products could not be separated by column chromatography.

Method C

The reaction was carried out as described in Method A above using copper (I) chloride in place of copper (II) acetate. The reaction was allowed to proceed at 0° C. for 5.5 hours. The proportion of the reagents was as follows: catechol (1 mmol), sodium iodate (4 mmol), copper (I) chloride (1 mmol), triethylamine (4 mmol), ethylenimine (4 mmol). After column chromatography this reaction method produced the title compound, 4,5-aziridinyl-1,2-benzoquinone (40 mg, 21% yield).

EXAMPLE 2

Preparation of 4,5-azetidinyl-1,2-benzoquinone

The synthetic procedure of Method A of Example 1 was generally followed to prepare the title compound. The reaction mixture consisted of the following reagents and proportions: catechol (1 mmol), azetidine (2.2 mmol), triethylamine (4 mmol), copper (I) chloride (1 mmol) and sodium iodate (4 mmol). The reaction carried out at 0° C. for 1 hour. The product was purified as described in Method A above to give 4,5-azetidinyl-1,2-benzoquinone (98.5 mg, 45% yield) as deep red needles from $CH_2Cl_2$/acetone (1:1), m.p. 138°–140° C. (decomp.); Found: C,65.73; H,6.48, N, 12.49; Anal. Calcd. for $C_{12}H_{14}N_2O_2$: C,66.03; H,6.46; N,12.83; I.R. $\upsilon$max 2960, 2890, 1640, 1570, 1540, 1430, 1340, 1300, 1220, 1140, 1070, 920, 910, 810, 770 $cm^{-1}$; U.V. $\lambda$max (95% EtOH) 236 nm (log $\epsilon$4.24), 369 (4.23), 520 (2.99); $^1$HNMR ($CDCl_3$) $\delta$, 2~2.6 (m, 4H, 2 $CH_2$), 3.8~4.2 (t, 8H, 2-$N(CH_2)_2$), 5.3 (s, 2H, 3,6-H).

EXAMPLE 3

Preparation of 4,5-pyrrolidinyl-1,2-benzoquinone

Method A

A method similar to that described in Method A of Example 1 was employed. The reaction mixture consisted of the following reagents and proportions: catechol (1 mmol), pyrrolidine (2.2 mmol), triethylamine (4.2 mmol), sodium iodate (8 mmol), copper (II) acetate (1 mmol). The reaction was allowed to proceed at 0° C. for 20 hours. After purification the product 4,5-pyrrolidinyl-1,2-benzoquinone (26.7 mg, 10.83% yield) was obtained as black red needles from $CH_2Cl_2$: acetone (1:1), mp 170°–172° C. (decomp.); Found: C=67.97, H=7.24, N=11.24; Anal. Calcd. for $C_{14}H_{18}N_2O_2$: C, 68.27; H=7.37, N=11.40%); I.R. $\upsilon$max 3060, 2960, 2840, 1610, 1560, 1510, 1470, 1440, 1290 $cm^{-1}$; U.V. $\lambda$max (95% EtOH) 250 nm (log $\epsilon$4.23), 371 (4.27); $^1$HNMR ($CDCl_3$) $\delta$ 2.1 (m, 8H, 2-$CH_2CH_2$-), 3.5 (m, 8H, 2-$N(CH_2)_2$), 5.6 (s, 2H, 3.6-H).

Method B

The synthetic procedure of Example 2 was generally followed. The reaction mixture consisted of the following reagents and proportions: catechol (1 mmol), pyrrolidine (2.2 mmol), triethylamine (4 mmol), sodium iodate (4 mmol), copper (I) chloride (1 mmol). The reaction was allowed to proceed at 0° C. for 2 hours and after purification gave the product 4,5-pyrrolidinyl-1,2-benzoquinone (114.4 mg, 46.4% yield).

EXAMPLE 4

Preparation of 4,5-bis-(dimethylamino)-1,2-benzoquinone

Method A

The synthetic procedure of Method A of Example 1 was generally followed to prepare the title compound. The reaction resulted in a crude product as black oil. Column chromatography with chloroformethyl acetate (4:1) elution gave 4,5-bis-(diethylamino)-1,2-benzoquinone (131 mg, 52.3% yield) which was recrystallized from $CH_2Cl_2$: acetone (1:1), mp 100°–103° C.; Found: C,66.89; H,8.86; N,10.95. Anal. Calcd. for $C_{14}H_{22}N_2O_2$: C,67.16; H,8.85; N,11.18%. I.R. $\upsilon$max 2980, 2940, 1630, 1530, 1360, 820 $cm^{-1}$; U.V. $\lambda$max (95% EtOH) 252 nm (log $\epsilon$4.19), 374 (4.23); $^1$HNMR ($CDCl_3$) $\delta$, 1.1 (t, 12H, 4 $CH_3$), 3.4 (q, 8H, 4 $CH_2$), 5.7 (s, 2H, 3, 6-H).

Method B

A similar reaction was carried out as in Method A of this Example 4 above, using copper (I) chloride in place of copper (II) acetate at 0° C. for 6.5 hours. The reaction provided the titled compound 4,5-diethylamino-1,2-benzoquinone was obtained in a yield of 40%.

EXAMPLE 5

Preparation of 4-chloroethylamino-5-methoxy-1,2-benzoquinone 4,5-Dimethoxy-1,2-benzoquinone (672.4 mg, 4 mmol) was dissolved in dichloromethane (40 ml) and stirred in a round-bottomed flask equipped with a cylindrical funnel from which a solution of chloroethylamine hydrochloride (1.2 g, 4.4 mmol) and triethylamine (2.4 ml, 16.8 mmol) in dichloromethane (50 ml) was added dropwise into the solution over the course of one hour. The reaction mixture was maintained with stirring at room temperature for 21 hours. After filtration, the remaining solution was washed with 10% hydrochloric acid, distilled water and then distilled water saturated with sodium chloride, and then dried over magnesium sulfate. Evaporation of the solvent gave the black red crude product. Column chromatography with chloroform: methanol (4:0.5, (v/v)) elution gave 4-chloroethylamino-5-methoxy-1,2-benzoquinone 274.3 mg, 31.8% yield) which was recrystallized from ethanol as red needles: mp 150°–152° C.; Found: C,50.17; H,4.77; N,6.44; Cl,16.39. Anal. Calcd. for $C_9H_{10}ClNO_3$: C,50.13; H,4.67; N,6.49; Cl,16.44%. I.R. $\upsilon$max 3400, 2940, 1660, 1640, 1620, 1580, 1510, 1250, 1180, 810 cm$^{-1}$. U.V. $\lambda$max (95% EtOH) 210 nm (log $\epsilon$4.35), 304 (4.23), 464 (3.51), $^1$HNMR (CDCl$_3$) $\delta$, 3.6 (m, 4H, NCH$_2$CH$_2$), 3.9 (S, 3H, O CH$_3$), 5.4 (S, 1H, 6-H), 5.7 (s, 1H, 3-H), 6.2 (br,s, 1H, NH).

EXAMPLE 6

In vitro Cytotoxicity Screen

As shown in Table I below, compounds of the invention exert an in vitro cytotoxicity effect under both normal oxygenation and hypoxia conditions. The following materials and procedures were employed in the screen to obtain the data set forth in Table I below.

Cell Line and Culture. The cell line used in the screen was EMT-6 mouse mammary tumor cells in culture that were maintained in exponential growth in Waymouth's medium (I.S.I. Corp., Chicago, Ill.), supplemented with 15% newborn calf serum, penicillin (100 units/ml), and streptomycin (100 μg/ml) (Grand Island Biological Co., Grand Island, N.Y.). The doubling time of these cultures, growing at 37° C. in a 5% CO$_2$/95% air atmosphere, was 16–19 hours. In vitro plating efficiencies of control cultures were 65–80%.

Production of Hypoxia. To produce hypoxia, plastic flasks, containing exponentially growing monolayers of tumor cells in complete medium plus serum, were fitted with sterile rubber septums and exposed to a continuously flowing 95% N$_2$/5% CO$_2$ humidified atmosphere for 4 hours at 37° C. as described by B. A. Teicher et al., *Int. J. Radiat. Oncol. Biol. Phy.*, 11:937–940 (1985); and B. A. Teicher et al., *Cancer Res.*, 41:73–81 (1981). Parallel flasks were maintained in 95% air/5% CO$_2$. At the end of 4 hours, the drug specified in Table I below was added to the flasks by injection through the rubber septum without disturbing the hypoxia.

pH Alterations. The pH of the medium was adjusted using a sodium bicarbonate (NaHCO$_3$)/5% CO$_2$ buffer system as described in L. E. Gerweck et al., *Radiat. Res.*, 70:224–235 (1977). For altered pH experiments, the flasks were purged with either 95% air/5% CO$_2$ 30 minutes before heating for normally oxygenated conditions or gassed with 95% N$_2$/5% CO$_2$ for 4 hours at 37° C. for hypoxic experiments as stated above. After completion of the drug treatment, the monolayers were washed with 0.9% phosphate-buffered saline, suspended by trypsinization, and plated in normal pH complete media for colony formation.

Drug Treatments. Exponentially growing cells were exposed to varying concentrations of the drugs specified in Table I below for 1 hour at 37° C. Non-drug-treated controls were handled identically. Drugs were prepared in sterile phosphate-buffered saline immediately before use and added to the cells in a small volume (50–100 μl). Addition of the drug solution did not significantly alter the pH of the culture. After treatment, the medium was removed, and the cultures were washed twice with phosphate buffered saline and suspended by trypsinization.

Cell Viability Measurements. Cell viability was measured by the ability of single cells to form colonies in vitro, as described by B. A. Teicher et al., *Int. J. Radiat. Oncol. Biol. Phys.*, 11:937–940 (1985); and B. A. Teicher et al., *Cancer Res.*, 41:73–81 (1981). Following treatment, suspensions of known cell numbers were plated in plastic Petri dishes and allowed to grow in a 37° C. incubator under standard culture conditions for 8–10 days. After this time interval, macroscopic colonies were stained with crystal violet in methanol containing 3.7% formaldehyde and were counted manually. Each experiment was repeated 3 times and each data point per experiment represents the results of 3 different dilutions of cells plated in triplicate. Results are shown in Table I below.

TABLE I

| Compound | Normal Oxygenation | | Hypoxia | |
|---|---|---|---|---|
| | IC$_{50}$, μM | IC$_{90}$, μM | IC$_{50}$, μM | IC$_{90}$, μM |
| 4,5-Aziridinyl-1,2-Benzoquinone | 0.4 | 1.1 | 0.2 | 1.0 |
| 4,5-Azetidinyl-1,2-Benzoquinone | 500 | >>500 | 400 | >>500 |
| 4,5-Pyrrolindinyl-1,2-Benzoquinone | >500 | >>500 | >500 | >>500 |
| 4,5-bis-(Diethyl-amino)-1,2-Benzoquinone | 500 | >>500 | 400 | >>500 |
| 4,5-Methoxy-1,2-Benzoquinone | 500 | >>500 | >>500 | >>500 |
| 4-Chloroethylamino-5-Methoxy-1,2-Benzoquinone | 125 | 455 | 110 | 190 |
| 3,6-bis-(Ethylcarboxy-amino)-2,5-Diaziridinyl-1,4-Benzoquinone (AZQ) | 5 | 15.5 | 7.5 | 17.5 |

EXAMPLE 7

In Vivo Antitumor Test Results

The in vivo potency of compounds of the invention is exemplified by the data set forth in Table II below. L1210 leukemia (10$^6$) cells were implanted intraperitoneally in DBA mice (Taconic Farms, Germantown, N.Y.) on day 0. Treatment with each drug was carried out daily for 5 days.

The drugs were administered intraperitoneally at the doses shown on Table II below. Each treatment group had six animals and the experiment was carried out twice. The percent increase-in-lifespan (% ILS) is for the treated subjects compared with the untreated controls.

TABLE II

| TREATMENT | DOSE, mg/kg[a] | SURVIVAL, DAYS[b] | % ILS |
|---|---|---|---|
| Control Group | — | 7.4 | — |
| Group treated with | 0.50 | 12.6 | 70 |
| 4,5-Aziridinyl-1,2- | 1.00 | 13.4 | 81 |
| Benzoquinone | 1.25 | 13.6 | 84 |
|  | 1.50 | 13.8 | 86 |
|  | 2.00 | 11.8 | 59 |
|  | 2.50 | 6.0 | toxic |
| Group treated with | 1.00 | 8.0 | 8 |
| 4,5-Azetidinyl-1,2- | 2.50 | 7.8 | 5 |
| Benzoquinone | 5.00 | 7.8 | 5 |
|  | 10.00 | 6.4 | toxic |
| Group treated with | 1.00 | 8.0 | 8 |
| 4,5-Pyrrolidinyl-1,2- | 2.50 | 8.0 | 8 |
| Benzoquinone | 5.00 | 7.6 | 3 |
|  | 10.00 | 6.3 | toxic |
| Group treated with | 1.00 | 7.8 | 5 |
| 4,5-Diethylamino- | 2.50 | 8.4 | 14 |
| 1,2-Benzoquinone | 5.00 | 8.6 | 16 |
|  | 10.00 | 7.8 | 5 |

[a]Drugs were administered i.p. daily on days 1–5.
[b]Life-span of the animals post tumor cell innoculation.

This invention has been described in detail with reference to preferred embodiments thereof. However, it will be appreciated that those skilled in the art, upon consideration of this disclosure, may make modification and improvements within the spirit and scope of the invention as set forth in the following claims.

What is claimed is:

1. A method for preparation of a 1,2-benzoquinone comprising:

contacting a catechol, an oxidant, a nucleophilic reagent, and a compound comprising a metal selected from the group consisting of Fe, Co, Ni, Cu, Zn, Ga, Ru, Rh and Pd in the presence of a basic catalyst for a time and temperature sufficient to form a 1,2-benzoquinone having the following formula:

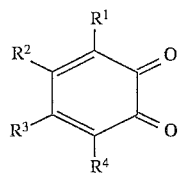

wherein $R^1$ and $R^4$ are each independently hydrogen, halogen, cyano, substituted or unsubstituted alkyl, substituted or unsubstituted alkenyl, substituted or unsubstituted alkoxy, substituted or unsubstituted aminoalkyl, or substituted or unsubstituted thioalkyl;

$R^2$ and $R^3$ are each independently hydrogen, halogen, cyano, substituted or unsubstituted alkyl, substituted or unsubstituted alkenyl, substituted or unsubstituted aminoalkyl, or substituted or unsubstituted thioalkyl, substituted or unsubstituted alkylsulfoxide, substituted or unsubstituted sulfonoalkyl, substituted or unsubstituted alkanoyl, substituted or unsubstituted alkylcarboxyamino, or a substituted or unsubstituted heteroaromatic group having 1 to 3 rings, 3 to 8 ring members in each ring and 1 to 3 N or S atoms, with at least one of $R^2$ and $R^3$ being other than hydrogen.

2. The method of claim 1 where the catechol, oxidant and compound comprising a metal is contacted with a nucleophilic reagent to form a 4,5-substituted-1,2-benzoquinone.

3. The method of claim 1 where the nucleophilic reagent comprises one or more N or S atoms.

4. The method of claim 1 where the nucleophilic reagent comprises one or more electron-attracting groups.

5. The method of claim 1 where the nucleophilic reagent is an organometallic reagent.

6. The method of claim 1 where the metal-containing compound comprises a metal selected from the group consisting of Fe, Co, Ni, Cu, Zn, and Ga.

7. The method of claim 1 where the metal-containing compound comprises Cu.

8. The method of claim 1 where the catechol, oxidant and compound comprising a metal are contacted at a temperature below room temperature.

9. The method of claim 1 where the catechol, oxidant and compound comprising a metal are contacted at a temperature between about −5° C. and 0° C.

10. The method of claim 1 where the substituted 1,2-benzoquinone is formed in a yield of about 40 percent or greater from the catechol.

11. The method of claim 1 wherein the catechol, oxidant, nucleophilic reagent and compound comprising a metal are contacted in the presence of a basic catalyst which is an organic amine.

12. The method of claim 1 wherein the nucleophilic reagent is a compound comprising a secondary aminoalkyl group.

13. The method of claim 1 wherein the nucleophilic reagent is a compound comprising a substituted or unsubstituted dialkylamino group.

14. The method of claim 1 wherein the nucleophilic reagent is a compound that comprises a heteroaromatic group or a heterocyclic group that comprises one or more nitrogen atoms.

15. A method for preparation of a 1,2-benzoquinone comprising:

contacting a catechol, an oxidant, a nucleophilic agent and a compound comprising Mn in the presence of a basic catalyst for a time and at a temperature sufficient to form a 1,2-benzoquinone having the formula

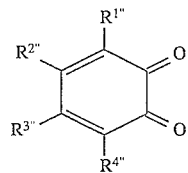

wherein $R^{1''}$ and $R^{4''}$ are each independently hydrogen, halogen, cyano, substituted or unsubstituted alkyl, substituted or unsubstituted alkenyl, substituted or unsubstituted alkoxy, substituted or unsubstituted aminoalkyl, or substituted or unsubstituted thioalkyl;

$R^{2''}$ and $R^{3''}$ are each independently hydrogen, substituted or unsubstituted alkyl, substituted or unsubstituted alkenyl, substituted or unsubstituted alkoxy, substituted or unsubstituted aminoalkyl, substituted or unsubstituted thioalkyl, substituted or unsubstituted alkylsulfoxide, substituted or unsubstituted sulfonoalkyl, substituted or unsubstituted alkanoyl, substituted or unsubstituted alkylcarboxyamino, or a substituted or unsubstituted heteroaromatic or heteroalicyclic group having 1 to 3 rings, 3 to 8 ring members in each ring and 1 to 3 hetero atoms, with at least one of $R^{2''}$ or $R^{3''}$ being selected from the group consisting of substituted or unsubstituted aminoalkyl, heteroaromatic group and heteroalicyclic group having at least one or more nitrogen atoms.

16. The method of claim 15 wherein the catechol, oxidant, nucleophilic reagent and Mn compound are contacted at a temperature between about −5° C. and 0° C.

17. The method of claim 15 wherein the nucleophilic reagent is a compound comprising a secondary aminoalkyl group.

18. The method of claim 15 wherein the nucleophilic reagent is a compound comprising a substituted or unsubstituted dialkylamino group.

19. The method of claim 16 wherein the nucleophilic reagent is a compound that comprises a moiety selected from the group of pyridyl, pyrazinyl, pyrroyl, pyrazole, imidazolyl, indolyl, pyridonal, aziridinyl, azetidinyl, pyrrolidino, 1,2,3,6-tetrahydropyridino, piperazino, piperidinyl, morpholino or thiomorpholino.

20. A method for preparation of a 1,2-benzoquinone substituted by a group other than hydrogen at the 4 and/or 5 positions comprising:

contacting a catechol, an oxidant, an amino-containing nucleophilic reagent, and a compound comprising Cu in the presence of a basic catalyst for a time and temperature sufficient to form the substituted 1,2-benzoquinone.

21. The method of claim 20 wherein the catechol, oxidant, nucleophilic reagent and Cu compound are contacted at a temperature between about −5° C. and 0° C.

22. The method of claim 20 wherein the catechol, oxidant, nucleophilic reagent and Cu compound are contacted in the presence of a basic catalyst which is an organic amine.

23. The method of claim 20 wherein the nucleophilic reagent is a compound comprising a secondary aminoalkyl group.

24. The method of claim 20 wherein the nucleophilic reagent is a compound comprising a substituted or unsubstituted dialkylamino group.

25. The method of claim 20 wherein the nucleophilic reagent is a compound that comprises a heteroaromatic group or a heterocyclic group that comprises one or more nitrogen atoms.

26. The method of claim 20 wherein the nucleophilic reagent is a compound that comprises a moiety selected from the group of pyridyl, pyrazinyl, pyrroyl, pyrazole, imidazolyl, indolyl, pyridonal, aziridinyl, azetidinyl, pyrrolidino, 1,2,3,6-tetrahydropyridino, piperazino, piperidinyl, morpholino or thiomorpholino.

27. A method for preparation of a 1.2-benzoquinone substituted by a group other than hydrogen at the 4 or 5 positions comprising:

contacting a catechol, an oxidant, a nucleophilic reagent other than an alkoxy compound or heteroaromatic compound comprising a nucleophilic oxygen atom, and a compound comprising a metal selected from the group consisting of Fe, Co, Ni, Cu, Zn, Ga, Ru, Rh and Pd in the presence of a basic catalyst for a time and temperature sufficient to form the substituted 1,2-benzoquinone.

28. The method of claim 27 wherein the catechol, oxidant, nucleophilic reagent and the compound comprising a metal are contacted in the presence of a basic catalyst which is an organic amine.

29. The method of claim 27 wherein the catechol, oxidant, nucleophilic reagent and the compound comprising a metal are contacted at a temperature between about −5° C. and 0° C.

30. A method for preparation of a 1,2-benzoquinone comprising:

contacting a catechol, an oxidant, and a compound comprising a metal selected from the group consisting of Fe, Co, Ni, Zn, Ga, Ru, Rh and Pd in the presence of a basic catalyst for a time and temperature sufficient to form the 1,2-benzoquinone.

31. The method of claim 30 wherein said 1,2-benzoquinone is substituted at the 4 and/or 5 positions.

32. A method for preparation of a 1,2-benzoquinone substituted at the 4 or 5 positions comprising:

contacting 1) a catechol, 2) an oxidant, 3) a nucleophilic reagent selected from the group consisting of substituted or unsubstituted aminoalkyl, substituted or unsubstituted thioalkyl, substituted or unsubstituted heteroaromatic or heteroalicyclic group having 1 to 3 rings, 3 to 8 ring members in each ring and 1 to 3 N or S atoms, alkyl groups substituted with one or more electron-attracting substituents and organometallic reagents, and 4) a compound comprising a metal selected from the group consisting of Fe, Co, Ni, Cu, Zn, Ga, Ru, Rh and Pd in the presence of a basic catalyst;

for a time and temperature sufficient to form the substituted 1,2-benzoquinone.

33. The method of claim 32 wherein the catechol, oxidant, nucleophilic reagent and the compound comprising a metal are contacted in the presence of a basic catalyst which is an organic amine.

34. The method of claim 32 wherein the catechol, oxidant, nucleophilic reagent and the compound comprising a metal are contacted at a temperature between about −5° C. and 0° C.

* * * * *